US006610719B2

(12) United States Patent
Paralkar et al.

(10) Patent No.: US 6,610,719 B2
(45) Date of Patent: Aug. 26, 2003

(54) USE OF PROSTAGLANDIN (PGE$_2$) RECEPTOR A (EP$_4$) SELECTIVE AGONISTS FOR THE TREATMENT OF ACUTE AND CHRONIC RENAL FAILURE

(75) Inventors: Vishwas M. Paralkar, Madison, CT (US); David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/771,164

(22) Filed: Jan. 29, 2001

(65) Prior Publication Data

US 2001/0041729 A1 Nov. 15, 2001

Related U.S. Application Data

(60) Provisional application No. 60/178,968, filed on Jan. 31, 2000.

(51) Int. Cl.$^7$ .......................... A61K 31/41; A61K 31/40

(52) U.S. Cl. ..................... 514/381; 514/352; 514/423; 514/573; 514/530

(58) Field of Search .............................. 514/381, 382, 514/423

(56) References Cited

U.S. PATENT DOCUMENTS

| | | | |
|---|---|---|---|
| 3,987,091 A | 10/1976 | Cragoe, Jr. et al. | 260/490 |
| 3,991,087 A | 11/1976 | Cragoe, Jr. et al. | 260/408 |
| 3,991,106 A | 11/1976 | Cragoe, Jr. et al. | 260/519 |
| 4,033,996 A | 7/1977 | Cragoe, Jr. et al. | 260/490 |
| 4,055,596 A | 10/1977 | Cragoe, Jr. et al. | 260/534 |
| 4,066,692 A | 1/1978 | Cragoe, Jr. et al. | 424/312 |
| 4,112,236 A | 9/1978 | Bicking et al. | 560/12 |
| 4,175,203 A | 11/1979 | Cragoe, Jr. et al. | 560/55 |
| 4,177,346 A | 12/1979 | Nelson | 542/427 |
| 5,605,814 A | 2/1997 | Abramovitz et al. | 435/69.1 |
| 5,716,835 A | 2/1998 | Regan et al. | 435/240.2 |
| 5,759,789 A | 6/1998 | Abramovitz et al. | 435/7.21 |
| 5,807,895 A | 9/1998 | Stratton et al. | 514/573 |
| 5,892,099 A | 4/1999 | Maruyama et al. | 560/121 |

FOREIGN PATENT DOCUMENTS

| | | | | |
|---|---|---|---|---|
| EP | 0855389 | 1/1998 | .......... | C07C/405/00 |
| EP | 0911321 | 4/1999 | .......... | C07C/311/13 |
| EP | 1080728 | 3/2001 | .......... | A61K/45/00 |
| EP | 1097922 | 5/2001 | .......... | C07C/405/00 |
| EP | 1114816 | 7/2001 | .......... | C07C/405/00 |
| GB | 1478281 | 6/1977 | .......... | C07C/59/00 |
| GB | 1479156 | 7/1977 | .......... | C07C/59/00 |
| GB | 1556569 | 11/1979 | .......... | C07D/207/26 |
| WO | WO 9828264 | 7/1998 | .......... | C07C/311/06 |
| WO | WO 9902164 | 4/1999 | .......... | A61K/31/557 |
| WO | WO 9919300 | 4/1999 | .......... | C07D/213/71 |
| WO | WO 9858911 | 12/1999 | .......... | C07C/405/00 |

OTHER PUBLICATIONS

CA 129:148850, Maruyama et al., Ep 855389, Jul. 19, 1998, abstract.*

Biosis PREV199900305555, Maruyama et al, US 5892099, Jun. 15, 1999, abstract.*

Biosis PREV199800326732, Breyer, Experimental Nephrology, 5–6/1998, 6(3), 180–188, abstract.*

The Merck manual, 15$^{th}$ edition, pp. 1566–1671, 1987.*

R. M. Breyer et al., American Journal of Physiology, vol. 270(3), pp. F485–F493 (1996), "Cloning and Expression of the Rabbit Prostaglandin Ep$_4$ Receptor. ".

R. Morath et al., The Journal of the American Society of Nephrology, vol. 10, pp. 1851–1860 (1999), "Immunolocalization of the Four Prostaglandin EP1, EP2, EP3, And EP4 in Human Kidney. ".

P. A. Zoretic et al., The Journal of Heterocyclic Chemictry, vol. 20, pp. 465–466 (1983), "Synthesis of (E)–7–[[2–[4–(m–Trifluoromethylphenoxy)–3α and 3β–Hydroxy–1–butenyl]–5–oxo–1–pyrrolidinyl]]heptanoic Acids. ".

L. Tang et al., Circulation Research, vol. 86(6) pp. 663–670, (Mar. 31, 2000), "Biphasic Actions of Prostaglandin E$_2$ on the Renal Afferent Arteriole Role of EP$_3$ and EP$_4$ Receptors". (published after Application's Priority date of Jan. 31, 2000).

George A. Porter, MD, The American Journal of Cardiology, vol. 64, pp. 22E–26E, 1989, "Contrast–Associated Nephropathy".

H. David Humes, et al., The Journal of Clinical Investigations, Inc., Dec. 1989, vol. 84, pp. 1757–1761, "Epidermal Growth Factor Enhances Renal Tubule Cell Regeneration and Repair and Accelerates the Recovery of Renal Function in Postischemic Acute Renal Failure".

Steven B. Miller et al., Proc. Natl. Acad. Sco. USA, vol. 89, pp. 11876–11880, Dec. 1992, "Insulin–like growth factor I accelerates recovery from ischemic acute tubular necrosis in the rat".

Steven B. Miller et al., The American Physiological Society, vol. 266, pp. F129–f134, 1994, "Hepatocyte growth factor accelerates recovery from acute ischemic renal injury in rats".

Slobodan Vukicevic, et al., J. Clin. Invest., vol. 102, No. 1, Jul. 1998, pp. 202–214, "Osteogenix Prorein–1 (Bone Morphogenetic Protin–7) Reduces Severity of Injury After Acute Renal Failure in Rat".

(List continued on next page.)

*Primary Examiner*—Rebecca Cook
(74) *Attorney, Agent, or Firm*—Peter C. Richardson; Gregg C. Benson; John A. Wichtowski

(57) ABSTRACT

This invention is directed to methods and compositions of treating acute or chronic renal failure or dysfunction, or conditions caused thereby, comprising administering prostaglandin agonists, which are EP$_4$ receptor selective prostaglandin agonists.

16 Claims, No Drawings

OTHER PUBLICATIONS

William B. Campbell, The Pharmacological Basis of Therapeutics, Eighth Edition, pp. 600–617, Chapter 24, "Lipid–Derived Autacoids: Eicosanoids and Platelet–Activating Factor".

W.S.S. Jee, et al., Bone, vol 21, No. 4, Oct 1997, pp. 297–304, "The In Vivo Anabolic Actions of Prostaglandins in Bone".

John B. Bicking, et al., Journal of Medicinal Chemistry, 1977, vol. 20, No. 1, pp. 35–43, "11, 12–Secoprostaglandins. 1. Acylhydroxyalkanoic Acids and Related Compounds".

James H. Jones, et al., Journal of Medicinal Chemistry, 1997, vol. 20, No. 1, pp. 44–48, "11, 12–Secoprostaglandins. 2. N–Acyl–N–alkyl–7–aminoheptanoic Acids".

John B. Bicking et al., Journal of Medicinal Chemistry, 1993, vol. 26, pp. 335–341, "11, 12–Secoprostaglandins. 6. Interphenylene Analogues of Acylhydroxyalkanoic Acids and Related Compounds as Renal Vasodilators".

John B. Bicking, et al., J. Med. Chem. 1983. vol. 26, pp. 342–348, "Prostaglandin Isosteres. 2. Chain–Modified Thiazolidinone Prostaglandin Analogues as Renal Vasodilators".

R.A. Lafaette, R.D. Perrone and A.S. Levey: "Laboratory Evaluation of Renal Function," in: *Diseases of the Kidney* (Eds: R.W. Schrier and C.W. Gottschalk), Little, Brown and Company, Inc., vol. 6, 307–354 (1998).

M.R. Hammerman and S.B. Miller, "Therapeutic Use of Growth Factors in Renal Failure," J. Am. Soc. Nephrolol., 5: 1–11 (1994).

R.C. Harris, "Growth Factors and Cytokines in Acute Renal failure, " Adv. Renal. Repl. Ther., 4: 43–53 (1997).

R.M. Breyer, et al., "Cloning and Expression of the Rabbit Prostaglandin $EP_4$ Receptor", The American Psychological Society, 270: pp. F485–F493, 1996.

M.D. Breyer, "Prostaglandin Receptors in the Kidney: A New Route for Intervention?", Experimental Nephrology, 1998;6:180–188.

R. Morath, et al., "Immunolocalization of the Four Prostaglandin $E_2$ Receptor Proteins EP1, EP2, EP3, and EP4 in Human Kidney", Journal of the American Society of Nephrology, 10: 1851–1860, 1999.

* cited by examiner

USE OF PROSTAGLANDIN (PGE$_2$) RECEPTOR A (EP$_4$) SELECTIVE AGONISTS FOR THE TREATMENT OF ACUTE AND CHRONIC RENAL FAILURE

CROSS REFERENCE TO RELATED APPLICATION

This application claims the benefit of U.S. Provisional Application No. 60/178,968, filed Jan. 31, 2000.

FIELD OF THE INVENTION

The present invention relates to methods and pharmaceutical compositions comprising receptor selective prostaglandin (PGE$_2$) agonists for the treatment of kidney diseases, such as chronic and acute renal failure or dysfunction, in animals, particularly mammals. More specifically, the present invention relates to such methods and pharmaceutical compositions comprising type 4 (EP$_4$) receptor selective prostaglandin (PGE$_2$) agonists.

BACKGROUND OF THE INVENTION

The naturally occurring prostaglandins are comprised of several biological entities including PBD, PGE, PGF, PGG, PGH and PGI. It has been well documented that prostaglandins have effects on many of the organs and systems of the body.

In the kidney, the prostaglandins modulate renal blood flow and may serve to regulate urine formation by both renovascular and tubular effects. In clinical studies, PGE, has been used to improve creatinine clearance in patients with chronic renal disease, to prevent graft rejection and cyclosporine toxicity in renal transplant patients, to reduce the urinary albumin excretion rate and N-acetyl-beta-D-glucosaminidase levels in patients with diabetic nephropathy, and to improve urea clearance in healthy volunteers. PGE$_1$ also has been administered intravenously during surgeries to prevent renal failure.

Renal dysfunction and/or renal failure is manifested in the body in a number of different ways. Any one or a combination of the following manifestations could indicate renal dysfunction or failure in a patient: lower than normal creatinine clearance; lower than normal free water clearance; higher than normal blood urea and/or nitrogen and/or potassium and/or creatinine levels; altered activity of kidney enzymes such as gamma glutamyl synthetase, alanine phosphatidase, N-acetyl-beta-D-glucosaminidase, or beta-2-microglobulin; altered urine osmolarity or volume; increase over normal levels or new observation of microalbuminuria or macroalbuminuria; or need for dialysis. Successful prevention of renal dysfunction or renal failure is indicated if the above described events do not occur at all, if they occur with less severity, if they occur in fewer patients at risk for renal dysfunction or renal failure; or if the patient recovers from these problems more quickly than normal.

Acute renal failure caused by the injection of contrast media has been recognized for many years as a complication of procedures utilizing such media. It has been estimated that the incidence of acute renal failure directly induced by contrast media is 10–15%, while the incidence of contrast associated nephropathy defined by clinically significant increases in serum creatinine is as high as 22%. See Porter, Am. J. Cardiol., 64: 22E-26E (1989). U.S. Pat. No. 5,807,895 discloses a method of preventing renal failure or dysfunction caused by medical procedures which utilize contrast media by intravenous administration of a prostaglandin compound selected from PGE$_1$, PGE$_2$ PGI$_2$ or an analog or pharmaceutically acceptable salt thereof.

Chronic renal failure (CRF) occurs as a result of progressive and later, permanent reduction in the glomerular filtration rate (GFR), which is associated with loss of functional nephron units. When the GFR continues to decline to less than 10% of normal (5–10 ml/min), the subject progresses to end-stage renal failure (ESRD). R. A. Lafayette, R. D. Perrone and A. S. Levey: "Laboratory Evaluation of Renal Function," in: *Diseases of the Kidney* (Eds: R. W. Schrier and C. W. Gottschalk), Little, Brown and Company, Inc., Vol. 6, 307–354 (1997). At this point, unless the subject receives renal replacement therapy (i.e., chronic hemodialysis, continued peritoneal dialysis or kidney transplantation) renal failure will rapidly progress to cause death. It is believed that the therapies which delay or halt the progression of ESRD will provide a basis for the treatment of chronic renal disease. A variety of growth and differentiation factors, for example, epidermal growth factor (EGF), transforming growth factor-α and -β (TGF-α and -β), insulin like growth factor-1 (IGF-1), fibroblast growth factor (FGF), platelet derived growth factor (PDGF) and bone morphogenetic protein (BMP) have been shown to participate in the regulation of the growth and repair of renal tissues. M. R. Hammerman and S. B. Miller, "Therapeutic Use of Growth Factors in Renal Failure," J. Am. Soc. Nephrolol., 5: 1–11 (1994); and R. C. Harris, "Growth Factors and Cytokines in Acute Renal Failure," Adv. Renal. Repl. Ther., 4: 43–53 (1997).

Epidermal growth factor (EGF) enhances renal tubule cell regeneration and repair and accelerates the recovery of renal function in postischemic acute renal failure. H. D. Humes, D. A. Cieslinski, T. Coimbra, J. M. Messana and C. Galvao, J. Clin. Invest., 84: 1757–1761 (1989). Insulin-like growth factor I (IGF-1) accelerates recovery from ischemic acute tubular necrosis in the rat. S. B. Miller, D. R. Martin, J. Kissane, and M. R. Hammerman, Proc. Natl. Acad. Sci. USA, 89:11876–11880 (1994). Hepatocyte growth factor accelerates recovery from acute ischemic renal injury in rats. S. B. Miller, D. R. Martin, J. Kissane, and M. R. Hammerman, Am. J. Physiol., 266:129–134 (1994). Osteogenic protein-1 (bone morphogenetic protein-7 (BMP-7)) reduces severity of injury after ischemic acute renal failure in the rat. S. Vukicevic, V. Basic, D. Rogic, N. Basic, M. S. Shih, A. Shepard, D. Jin et al., J. Clin. Invest., 102: 202–214 (1998).

The term prostaglandin refers to compounds which are analogs of the natural prostaglandins PGD$_1$, PGD$_2$, PGE$_2$, PGE$_1$ and PGF$_2$. These compounds bind to the prostaglandin receptors. Such binding is readily determined by those skilled in the art according to standard assays (e.g., S. An et al., Cloning and Expression of the EP$_2$ Subtype of Human Receptors for Prostaglandin E$_2$, Biochemical and Biophysical Research Communications, 197(1): 263–270 (1993)). These compounds can be synthesized by methods known in the art. See, e.g., Goodman and Gilman, *The Pharmacological Basis of Therapeutics*, Eighth Ed., Pergamon Press, pp. 601–604 (1990).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while PGE$_2$ contains a trans unsaturated double bond at the $C_{13}$–$C_{14}$ and a cis double bond at the $C_5$–$C_6$ position. However, there are severe side effects associated with $PGE_2$ treatment. W. S. S. Jee and Y. F. Ma, Bone, 21:297–304 (1997).

A variety of prostaglandins are described and referenced below. However, other prostaglandins will be known to those skilled in the art.

U.S. Pat. No. 4,177,346 discloses certain 1,5-disubstituted-2-pyrrolidones which are prostaglandin-like in chemical structure and have vasodilator activity, antihypertensive activity and antisecretory activity.

International Patent Application, Publication No. WO 99/02164, discloses methods and compositions for treating impotence or erectile dysfunction by using prostaglandins that are selective $EP_2$ or $EP_4$ prostanoid receptor agaonists.

U.S. Pat. No. 4,112,236 discloses certain interphenylene 8-aza-9-dioxothia-11,12-secoprostaglandins which have renal vasodilatory activity and are useful for the treatment of patients with renal impairment. U.S. Pat. No. 4,033,996 discloses certain 8-aza-9-oxo(and dioxo)-thia-11,12-secoprostaglandins which are useful as renal vasodilators, for the prevention of thrombus formation, to induce growth hormone release, and as regulators of the immune response.

Certain 11,12-secoprostaglandins and analogs thereof, which have a variety of therapeutic uses, including their use as renal vasodilators, are disclosed, for example, in the following: Great Britain Patent Nos. 1 478 281 and 1 479 156; U.S. Pat. Nos. 3,987,091; 3,991,087; 3,991,106; 4,055, 596; 4,066,692; and 4,175,203; J. B. Bicking et al., J. Med. Chem., 1977, Vol. 20, No. 1, pages 3543; J. H. Jones et al., J. Med. Chem., 1977, Vol. 20, No. 1, pages 4448; J. B. Bicking et al., J. Med. Chem., 1983, Vol. 26, pages 335–341; and J. B. Bicking et al., J. Med. Chem., 1983, Vol. 26, pages 342–348.

European Patent Application, Publication No. EP 0 911 321, and International Patent Applications, Publication Nos. WO 99/19300, WO 98/28264 and WO 98/58911, disclose certain prostaglandin agonists for the treatment of a variety of bone disorders, including osteoporosis, and for kidney degeneration.

Thus, there is a continuing need and a continuing search in this field of art for therapies for treating renal failure or dysfunction. More specifically, there is a need for receptor selective prostaglandin therapies, which do not have the side effects caused by non-selective agents.

SUMMARY OF THE INVENTION

The present invention particularly provides methods of treating acute or chronic renal failure or dysfunction, or a condition asociated therewith, in a mammal comprising administering to said mammal an $EP_4$ receptor selective agonist, an isomer thereof, a prodrug of said agonist or isomer, or a pharmaceutically acceptable salt of said agonist, isomer or prodrug. More particularly, the present invention provides said methods wherein said condition is selected from the group consisting of hypertension, congestive heart failure, glomerulonephritis, uremia and chronic renal insufficiency.

Also, the present invention particularly provides methods of using a pharmaceutical composition comprising a compound which is a selective $EP_4$ receptor agonist, an isomer thereof, a prodrug of said agonist or isomer, or a pharmaceutically acceptable salt of said agonist, isomer or prodrug, together with a physiologically acceptable diluent, carrier or vehicle, for the treatment of acute or chronic renal failure or dysfunction, or a condition caused thereby, in a mammal. More particularly, the present invention provides said methods wherein said condition is selected from the group consisting of hypertension, congestive heart failure, glomerulonephritis, uremia and chronic renal insufficiency.

The term "prostaglandin agonist" refers to a compound, including its isomers, prodrugs and pharmaceutically acceptable salts, which binds to a prostaglandin receptor, such as $EP_4$, and mimics the action of the prostaglandin in vivo. A variety of such compounds are described and referenced above. However, other prostaglandin agonists will be known to those skilled in the art.

Preferred $EP_4$ selective agonists for use in the present invention include compounds of formula I:

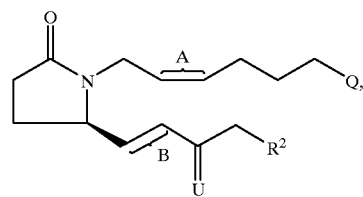

I prodrugs thereof or pharmaceutically acceptable salts of said compounds or said prodrugs, wherein:

Q is $COOR^3$, $CONHR^4$ or tetrazol-5-yl;
A is a single or cis double bond;
B is a single or trans double bond;
U is

$R^2$ is α-thienyl, phenyl, phenoxy, monosubstituted phenyl or monosubstituted phenoxy, said substituents being selected from the group consisting of chloro, fluoro, phenyl, methoxy, trifluoromethyl and ($C_1$–$C_3$)alkyl;
$R^3$ is hydrogen, ($C_1$–$C_5$)alkyl, phenyl or p-biphenyl;
$R^4$ is $COR^5$ or $SO_2R^5$; and
$R^5$ is phenyl or ($C_1$–$C_5$)alkyl.

The compounds of formula I may be prepared as disclosed in commonly assigned U.S. Pat. No. 4,177,346, which is hereby incorporated by reference herein.

A preferred group of $EP_4$ receptor selective agonists of formula I are those compounds of formula I wherein Q is 5-tetrazolyl. Particularly preferred compounds within this group include 5-(3-hydroxy-4-phenyl-but-1-enyl)-1-[6-(1H-tetrazol-5-yl)-hexyl]-pyrrolidin-2-one and 5-(3-hydroxy-4-phenyl-butyl)-1-[6-(1H-tetrazol-5-yl)-hexyl]-pyrrolidin-2-one.

Another preferred group of $EP_4$ receptor selective agonists of formula I are those compounds of formula I wherein Q is COOH. Particularly preferred compounds within this group include 7-[2-(3-hydroxy-4-phenyl-but-1-enyl)-5-oxo-pyrrolidin-1-yl]-heptanoic acid and 7-(2-(3-hydroxy-4-phenyl-butyl)-5-oxo-pyrrolidin-1-yl)-heptanoic acid.

The term "treating", "treat" or "treatment" as used herein includes preventative (e.g., prophylactic), palliative and curative treatment.

The term "pharmaceutically acceptable" means the carrier, vehicle, diluent, excipients, and/or salt must be compatible with the other ingredients of the formulation, and not deleterious to the recipient thereof.

The expression "prodrug" refers to a compounds that is a drug precursor which, following administration, releases the drug in vivo via some chemical or physiological process (e.g., a prodrug on reaching the physiological pH or through enzyme action is converted to the desired drug form). Exemplary prodrugs upon cleavage release the corresponding drug compounds.

The expression "pharmaceutically acceptable salt" refers to nontoxic anionic salts containing anions such as, but not limited to, chloride, bromide, iodide, sulfate, bisulfate, phosphate, acetate, maleate, fumarate, oxalate, lactate, tartrate, citrate, gluconate, methanesulfonate and 4-toluenesulfonate. The expression also refers to nontoxic cationic salts such as, but not limited to, sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine and tromethamine (2-amino-2-hydroxymethyl-1,3-propanediol).

Other features and advantages will be apparent from the description and the appendant claims which describe the present invention.

DETAILED DESCRIPTION OF THE INVENTION

Any $EP_4$ receptor selective agonist may be used as the $EP_4$ receptor selective agonist of this invention. $EP_4$ selective agonists are compounds which have an $IC_{50}$ at the $EP_1$, $EP_2$ and $EP_3$ receptor which is at least 10-fold greater than the $IC_{50}$ at the $EP_4$ receptor subtype. For example, 7-(2-(3-hydroxy-4-phenyl-butyl)-5-oxo-pyrrolidin-1-yl)-heptanoic acid is an $EP_4$ receptor selective $PGE_2$ agonist with an $EP_4$ receptor binding $IC_{50}$ of 16 nM. At all other EP receptor subtypes, including the $EP_1$, $EP_2$ and $EP_3$ receptor subtypes, the $IC_{50}$ for 7-(2-(3-hydroxy-4-phenyl-butyl)-5-oxo-pyrrolidin-1-yl)-heptanoic acid is greater than 3200 nM.

Accordingly, high selectivity or specificity for the $EP_4$ receptor, compared to other prostaglandin receptors, characterizes the compounds to be used in the methods and compositions according to the present invention. The more specific the compound is for the $EP_4$ receptor, the better are the therapeutic results that are obtained in the methods and compositions according to the present invention. Also, the receptor selectivity of the compounds to be used in the methods and compositions of the present invention results in the lessening or elimination of undesirable side effects caused by nonselective agents.

The $EP_4$ receptor selective agonists used in the methods of this invention can be adapted to therapeutic use in animals, e.g., mammals, and particularly humans. These compounds exhibit renal vasodilatory activity, and, therefore, are useful for the treatment of patients with renal impairment. Included in this group are patients with hypertension, renal failure, diabetes-induced renal failure, congestive heart failure, glomerulonephritis, uremia, and chronic renal insufficiency. These compounds by virtue of their renal vasodilatory activity improve renal function.

The utility of the $EP_4$ selective agonists used in the methods of the present invention as medical agents in the treatment of acute or chronic renal failure or dysfunction in animals, e.g., mammals, especially humans, is demonstrated by the activity of those agonists in conventional assays, including the prostaglandin receptor binding assay, the cyclic AMP assay, and in vivo assays, including the acute renal failure assays, all of which are described below. Such assays also provide a means whereby the activities of the $EP_4$ selective agonists can be compared to each other and with the activities of other known compounds and compositions. The results of these comparisons are useful for determining dosage levels in animals, e.g., mammals, including humans, for the treatment of such diseases.

Determination of cAMP Elevation in 293-S Cell Lines Stably Overexpressing Recombinant Human $EP_4$ Receptors cDNA representing the complete open reading frame of the human $EP_4$ receptor is generated by reverse transcriptase polymerase chain reaction using oligonucleotide primers based on published sequences (J. W. Regan, T. J. Bailey, D. J. Pepperl, K. L. Pierce, A. M. Bogardus, J. E. Donello, C. E. Fairbairn, K. M. Kedzie, D. F. Woodward and D. W. Gil, "Cloning of a Novel Human Prostaglandin Receptor with Characteristics of the Pharmacologically Defined $EP_2$ Subtype," Mol. Pharmacology 46:213–220 (1994)) and RNA from primary human lung cells ($EP_4$) as templates. cDNAs are cloned into the multiple cloning site of pcDNA3 (Invitrogen Corporation, 3985B Sorrento Valley Blvd., San Diego, Calif. 92121) and used to transfect 293-S human embryonic kidney cells via calcium phosphate co-precipitation. G418-resistant colonies are expanded and tested for specific [$^3$H]$PGE_2$ binding. Transfectants demonstrating high levels of specific [$^3$H]$PGE_2$ binding are further characterized by Scatchard analysis to determine $B_{max}$ and $K_d$s for $PGE_2$. The lines selected for compound screening have approximately 256,400 receptors per cell and a $K_d$=2.9 nM for $PGE_2$ ($EP_4$). Constitutive expression of the receptor in parental 293-S cells is negligible. Cells are maintained in RPMI supplemented with fetal bovine serum (10% final) and G418 (700 ug/ml final).

cAMP responses in the 293-S/$EP_4$ lines are determined by detaching cells from culture flasks in 1 ml of Ca++ and Mg++ deficient PBS via vigorous pounding, adding serum-free RPMI to a final concentration of 1×10$^6$ cells/ml, and adding 3-isobutyl-1-methylxanthine (IBMX) to a final concentration of 1 mM. One milliliter of cell suspension is immediately aliquoted into individual 2 ml screwcap microcentrifuge tubes and incubated for 10 minutes, uncovered, at 37° C., 5% $CO_2$, 95% relative humdity. The compound to be tested in DMSO or ethanol is then added to cells at 1:100 dilutions such that final DMSO or ethanol concentrations is 1%. Immediately after adding compound, the tubes are covered, mixed by inverting two times, and incubated at 37° C. for 12 minutes. Samples are then lysed by incubation at 100° C. for 10 minutes and immediately cooled on ice for 5 minutes. Cellular debris is pelleted by centrifugation at 1000×g for 5 minutes, and cleared lysates are transferred to fresh tubes. cAMP concentrations are determined using a commercially available cAMP radioimmunoassay (RIA) kit (NEK-033, DuPont/NEN Research Products, 549 Albany St., Boston, Mass. 02118) after diluting cleared lysates 1:10 in cAMP RIA assay buffer (included in kit). Typically, the cells are treated with 6–8 concentrations of the compound to be tested in 1 log increments. $EC_{50}$ calculations are performed on a calculator using linear regression analysis on the linear portion of the dose response curves.

Assay for Binding to Prostaglandin $E_2$

Membrane Preparation:

All operations are performed at 4° C. Transfected cells expressing prostaglandin $E_2$ type 1 receptors ($EP_1$), type 2 ($EP_2$), type 3 ($EP_3$) or type 4 ($EP_4$) receptors are harvested and suspended to 2 million cells per ml in Buffer A [which is composed of the following: 50 mM Tris-HCl (pH 7.4), 10 mM $MgCl_2$, 1 mM EDTA, 1 mM Pefabloc peptide (Boehringer Mannheim Corp., Indianapolis, Ind.), 10 $\mu$M Phosporamidon peptide (Sigma, St. Louis, Mo.), 1 $\mu$M pepstatin A peptide (Sigma, St. Louis, Mo.), 10 $\mu$M elastatinal peptide (Sigma, St. Louis, Mo.), and 100 $\mu$M antipain peptide (Sigma, St. Louis, Mo.)]. The cells are lysed by sonification with a Branson Sonifier (Model #250, Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3–10 mg of protein per ml of Buffer A, the protein concentration being determined by the method of Bradford [M. Bradford, Anal. Biochem., 72, 248 (1976)]. Resuspended membranes are then stored frozen at −80° C. until use.

Binding Assay:

Frozen membranes prepared as above are thawed and diluted to 1 mg protein per ml in Buffer A above. One volume of membrane preparation is combined with 0.05 volume test compound or buffer and one volume of 3 nM $^3$H-prostaglandin $E_2$ (#TRK 431, Amersham, Arlington Heights, Ill.) in Buffer A. The mixture (205 $\mu$L total volume) is incubated for 1 hour at 25° C. The membranes are then recovered by filtration through type GF/C glass fiber filters (#1205–401, Wallac, Gaithersburg, Md.) using a Tomtec harvester (Model Mach 11/96, Tomtec, Orange, Conn.). The membranes with bound $^3$H-prostaglandin $E_2$ are trapped by the filter, while the buffer and unbound $^3$H-prostaglandin $E_2$ pass through the filter into waste. Each sample is then washed 3 times with 3 ml of 50 mM Tris-HCl (pH 7.4), 10 mM $MgCl_2$, and 1 mM EDTA. The filters are then dried by heating in a microwave oven. To determine the amount of $^3$H-prostaglandin bound to the membranes, the dried filters are placed into plastic bags with scintillation fluid and counted in a LKB 1205 Betaplate reader (Wallac, Gaithersburg, Md.). $IC_{50}$s are determined from the concentration of test compound required to displace 50% of the specifically bound $^3$H-prostaglandin $E_2$.

The full length coding sequence for the $EP_1$ receptor is made as disclosed in Funk et al., Journal of Biological Chemistry, 1993, 268, 26767–26772. The full length coding sequence for the $EP_2$ receptor is made as disclosed in Regan et al., Molecular Pharmacology, 1994, 46, 213–220. The full length coding sequence for the $EP_3$ receptor is made as disclosed in Regan et al., British Journal of Pharmacology, 1994, 112, 377–385. The full length coding sequence for the $EP_4$ receptor is made as disclosed in Bastien, Journal of Biological Chemistry, 269: 11873–11877 (1994). These full length receptors are used to prepare 293S cells expressing the $EP_1$, $EP_2$, $EP_3$ and $EP_4$ receptors. Additional information on the human $EP_2$ and human $EP_4$ prostaglandin receptors is disclosed in U.S. Pat. Nos. 5,605,814; 5,716,835; and 5,759,789; which are hereby incorporated by reference herein.

293S cells expressing one of the human $EP_1$, $EP_2$, $EP_3$ or $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR reaction using the total RNA from human kidney (for $EP_1$), human lung (for $EP_2$), human lung (for $EP_3$) or human lymphocytes (for $EP_4$) as a source. PCR products are cloned by the TA overhang method into pCR2.1 (Invitrogen, Carlsbad, Calif.) and identity of the cloned receptor is confirmed by DNA sequencing.

293S cells (Mayo, Dept. of Biochemistry, Northwestern Univ.) are transfected with the cloned receptor in pcDNA3 (Invitrogen Corporation, 3985B Sorrento Valley Blvd., San Diego, Calif. 92121) by electroporation. Stable cell lines expressing the receptor are established following selection of transfected cells with G418.

Clonal cell lines expressing the maximal number of receptors are chosen following a whole cell $^3$H-$PGE_2$ binding assay using unlabeled $PGE_2$ as a competitor.

Acute Renal Failure Rat Model

The remnant rat kidney (5/6 nephrectomy) model employed was essentially as previously described in the literature (Vukicevic et al., Journal of Bone and Mineral Research, 2:533–545 (1987)). In brief, male rats (4 months old, weighing approximately 400 g) were anesthesized by intraperitoneal administration of ketamin (20 mg/kg) and then subjected to unilateral nephrectomy (left kidney). All animals were subjected to intraperitoneal administration of 1–3 ml of prewarmed saline to compensate for any fluid loss during the surgery. After one week, ⅔ of the remaining kidney was surgically removed. The rats were allowed to recover for one or two weeks prior to the initiation of the therapy for the prevention of the disease. The rats were pair fed to comparable weight for control and treated animals. The 5/6 nephrectomy model has been shown to reproduce several features of progressive human renal disease; namely, glomerulosciersosis, tubulointerstitial disease, proteinuria, progressive decline in kidney function and the development of systemic hypertension.

Blood samples (0.5 ml) were obtained from the orbital plexus and serum creatinine, BUN (blood urea nitrogen), calcium, phosphate and other blood chemistries were monitored throughout the study. Urine was collected on metabolic cages for 24 h. Creatinine was measured by a Jaffe method. A. W. Whelton, A. J. Watson and R. C. Rock: "Nitrogen Metabolites and Renal Function," in: *Clinical Chemistry* (Eds: C. A. Burtis and E. R. Ashwood) W. B. Saunders, Philadelphia, Pa., 1513–1575 (1994). BUN was measured by a glutamate dehydrogenase ultraviolet method, phosphorus by a molybdate method, and calcium by an o-cresolphtaleine method. R. A. Lafayette, R. D. Perrone and A. S. Levey: "Laboratory Evaluation of Renal Function," in: *Diseases of the Kidney* (Eds: R. W. Schrier and C. W. Gottschalk), Little, Brown and Company, Inc., Vol. 6, 307–354 (1997). The GFR was calculated using serum creatinine over urine creatinine (24 hr collection) and adjusted to body weights. The cumulative survival rate was also observed and recorded for both the control and the experimental groups. The kidney was subjected to histomorphometric analysis and scored for tissue pathology.

Results: The efficacy of 7-(2-(3-hydroxy-4-phenyl-butyl)-5-oxo-pyrrolidin-1-yl)-heptanoic acid, an $EP_4$ receptor selective $PGE_2$ agonist of the present invention, was tested in pre-clinical models of acute renal failure. Two different models of acute renal failure were used: the nephrotoxic acute renal failure model, as described above, and the reperfusion renal injury model, which involved clamping both renal arteries for 60 minutes. (K. J. Kelly, W. W. Williams, R. B. Colvin and J. V. Bonventure, "Intercellular Adhesion Molecule 1 Protects the Kidney Against Ischemic Injury," Proc. Natl. Acad. Sci. USA, 91:812–816 (1994); and S. Vukicevic, V. Basic, D. Rogic, N. Basic, M. S. Shih, A. Shepard, D. Jin, D. Bosukonda, W. Jones, H. Dorai, S. Ryan, D. Griffiths, J. Maliakal, M. Jelic, M. Pastorcic, A. Stavljenic and K. Sampath, "Osteogenic Protein-1 (Bone Morphogenetic Protein-7) Reduces Severity of Injury After Ischemic Acute Renal Failure in Rat," J. Clin. Invest.,102:202–214 (1998).)

In the nephrotoxic acute renal failure model, the $EP_4$ agonist was effective in protecting against renal injury, based on serum parameters, and increased the survival time of animals in a dose dependent manner, with a dose of 10 mg/kg being better than the dose of 1 mg/kg. In this study, four out of ten animals survived in the control group after seven days, whereas nine out of ten animals survived in the treated group at a dose of 10 mg/kg. In the reperfusion renal injury model, the $EP_4$ agonist was effective 24 hours following reperfusion. The animals were dosed with the $EP_4$ agonist just prior to the initiation of the nephrotoxic insult.

Administration of an $EP_4$ receptor selective agonist according to the methods of this invention can be via any available mode which delivers the $EP_4$ receptor selective agonist systemically or locally. These methods include oral routes, parenteral, intraduodenal routes, etc. Generally, the compounds of this invention are administered orally, but parenteral administration (e.g., intravenous, intramuscular, transdermal, subcutaneous, rectal or intramedullar) may be utilized, for example, where oral administration is inappropriate for the target or where the patient is unable to ingest the drug.

In any event, the amount and timing of the compound administered will, of course, be dependent on the subject being treated, on the severity of the affliction, on the manner of administration and on the judgment of the prescribing physician. Thus, because of patient to patient variability, the dosages given herein are a guideline and the physician may titrate doses of the drug compound to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

The $EP_4$ receptor selective agonist compounds used in the methods of this invention are generally administered in the form of a pharmaceutical composition comprising at least one of the compounds of this invention together with a pharmaceutically acceptable vehicle or diluent. Thus, the $EP_4$ receptor selective agonist compound can be administered individually in any conventional form, such as oral, intranasal, parenteral, rectal or transdermal dosage form.

For oral administration the pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compositions of this invention can be combined with various sweetening agents, flavoring agents, coloring agents, emulsifying agents and/or suspending agents, as well as such diluents as water, ethanol, propylene glycol, glycerin and various like combinations thereof.

The compounds can also be administered orally in solid solution with lipids such as cholesterol acetate. The inclusion of lipid in the formulation markedly increases absorption of the compound or analog. Preparation of such formulations is described in detail in Rudel, U.S. Pat. No. 3,828,106, which is incorporated herein by reference.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Compositions to be administered intravenously or by injection can be prepared as solutions of the compound in, for example, an isotonic aqueous solution, an alcohol solution, an ethanol-saline solution, or an ethanol-dextrose solution. Ethanol can be added to the solution to increase solubility and other additives such as methylparaben or other ingredients such as fillers, colorings, flavorings, diluents and the like can be included. The composition can also be administered as a suspension of the compound or analog in aqueous or non-aqueous media.

Among the preferred formulations for administration intravenously or by injection are complexes of the active ingredient with α-cyclodextrin. Preparation of complexes of compounds and analogs with α-cyclodextrin clathrates are described in detail in Hayashi et al., U.S. Pat. No. 4,054,736, which is incorporated herein by reference. Complexes wherein the ratio of α-cyclodextrin to a compound of this invention is 97:3 are especially preferred.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in the art. For examples of methods of preparing pharmaceutical compositions, see *Remington's Pharmaceutical Sciences*, Mack Publishing Company, Easton, Pa., 19th Edition (1995). Thus, as described above, while the compounds of this invention may be administered to the patients in any of the known formulations or modes of administration.

A preferred dosage for the methods and compositions of the present invention is about 0.001 to about 100 mg/kg/day of an $EP_4$ receptor selective agonist, an isomer thereof, a prodrug of said agonist or isomer, or a pharmaceutically acceptable salt of said agonist, isomer or prodrug. An especially preferred dosage is about 0.01 to about 10 mg/kg/day of an $EP_4$ receptor selective agonist, an isomer thereof, a prodrug of said agonist or isomer or a pharmaceutically acceptable salt of said agonist, isomer or prodrug.

More specifically, for administration intravenously or by injection, the dosages of the compounds to be used in the methods and compositions of the present invention can range from about 5 to about 60 ng/min/kg body weight, with the preferred dosage range being from about 10 ng/kg/min to about 30 ng/kg/min. If the dose is administered by intravenous injection, it should not exceed about 100 μg/kg body weight per day.

What is claimed is:

1. A method of treating acute or chronic renal failure or dysfunction in a mammal comprising administering to said mammal about 0.001 mg/kg/day to about 100 mg/kg/day of an $EP_4$ receptor selective agonist, an isomer thereof, a prodrug of said agonist or isomer, or a pharmaceutically acceptable salt of said agonist, isomer or prodrug, provided said acute or chronic renal dysfunction is not nephritis and further provided said acute or chronic renal failure or dysfunction is not the result of hypertension.

2. A method of treating acute or chronic renal failure or dysfunction in a mammal comprising administering to said mammal about 0.001 mg/kg/day to about 100 mg/kg/day of an $EP_4$ receptor selective agonist of formula I:

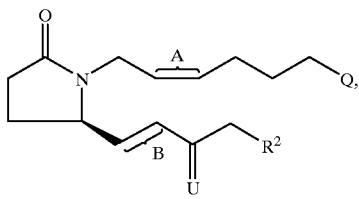

an isomer thereof, a prodrug of said agonist or isomer, or a pharmaceutically acceptable salt of said agonist, isomer or prodrug, wherein:

Q is $COOR^3$, $CONHR^4$ or tetrazol-5-yl;

A is a single or cis double bond;

B is a single or trans double bond;

=U is

$R^2$ is α-thienyl, phenyl, phenoxy, monosubstituted phenyl or monosubstituted phenoxy, said substituents being selected from the group consisting of chloro, fluoro, phenyl, methoxy, trifluoromethyl and $(C_1-C_3)$alkyl;

$R^3$ is hydrogen, $(C_1-C_5)$alkyl, phenyl or p-biphenyl;

$R^4$ is $COR^5$ or $SO_2R^5$; and $R^5$ is phenyl or $(C_1-C_5)$alkyl.

3. The method of claim 2 wherein Q is tetrazol-5-yl.

4. The method of claim 3 wherein the $EP_4$ receptor selective agonist of formula us 5-(3-hydroxy-4-phenyl-but-1-enyl)-1-[6-(1H-tetrazol-5-yl)-hexyl]-pyrrolidin-2-one.

5. The method of claim 3 wherein the $EP_4$ receptor selective agonist is 5-(3-hydroxy-4-phenyl-butyl)-1-[6-(1H-tetrazol-5-yl)-hexyl]-pyrrolidin-2-one.

6. The method of claim 2 wherein Q is $COOR^3$ and $R^3$ is hydrogen.

7. The method of claim 6 wherein the $EP_4$ receptor selective agonist of formula is 7-(2-(3-hydroxy-4-phenyl-butyl)-5-oxo-pyrrolidin-1-yl)-heptanoic acid.

8. The method of claim 6 wherein the $EP_4$ receptor selective agonist of formula us 7-[2-(3-hydroxy-4-phenyl-but-1-enyl)-5-oxo-pyrrolidin-1-yl]-heptanoic acid.

9. A method of treating acute or chronic renal failure or dysfunction in a mammal comprising administering to said mammal a pharmaceutical composition, said composition comprising about 0.001 mg/kg/day to about 100 mg/kg/day of a selective $EP_4$ receptor agonist, an isomer thereof, a prodrug of said agonist or isomer, or a pharmaceutically acceptable salt of said agonist, isomer or prodrug, together with a physiologically acceptable diluent, carrier or vehicle, provided said acute or chronic renal dysfunction is not nephritis and further provided said acute or chronic renal failure or dysfunction is not the result of hypertension.

10. A method of treating acute or chronic renal failure or dysfunction in a mammal comprising administering to said mammal a pharmaceutical composition, said composition comprising about 0.001 mg/kg/day to about 100 mg/kg/day of an $EP_4$ receptor selective agonist of formula I:

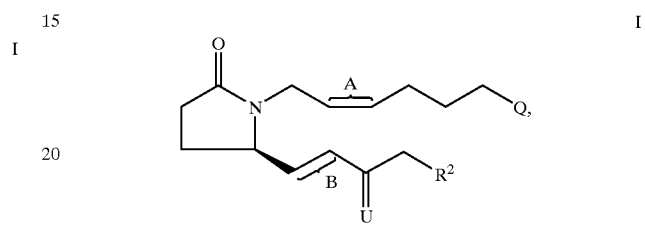

an isomer thereof, a prodrug of said agonist or isomer, or a pharmaceutically acceptable salt of said agonist, isomer or prodrug, wherein:

Q is $COOR^3$, $CONHR^4$ or tetrazol-5-yl;

A is a single or cis double bond;

B is a single or trans double bond;

=U is

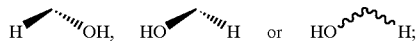

$R^2$ is α-thienyl, phenyl, phenoxy, monosubstituted phenyl or monosubstituted phenoxy, said substituents being selected from the group consisting of chloro, fluoro, phenyl, methoxy, trifluoromethyl and $(C_1-C_3)$alkyl;

$R^3$ is hydrogen, $(C_1-C_5)$alkyl, phenyl or p-biphenyl;

$R^4$ is $COR^5$ or $SO_2R^5$; and $R^5$ is phenyl or $(C_1-C_5)$alkyl, together with a physiologically acceptable diluent, carrier or vehicle.

11. The method of claim 10 wherein Q is tetrazol-5-yl.

12. The method of claim 11 wherein the $EP_4$ receptor selective agonist of formula I is 5-(3-hydroxy-4-phenyl-but-1-enyl)-1-[6-(1H-tetrazol-5-yl)-hexyl]-pyrrolidin-2-one.

13. The method of claim 11 wherein the $EP_4$ receptor selective agonist of formula I is 5-(3-hydroxy-4-phenyl-butyl)-1-[6-(H-tetrazol-5-yl)-hexyl]-pyrrolidin-2-one.

14. The method of claim 10 wherein Q is $COOR^3$ and $R^3$ is hydrogen.

15. The method of claim 14 wherein the $EP_4$ receptor selective agonist of formula I is 7-(2-(3-hydroxy-4-phenyl-butyl)-5-oxo-pyrrolidin-1-yl)-heptanoic acid.

16. The method of claim 14 wherein the $EP_4$ receptor selective agonist of formula I is 7-[2-(3-hydroxy-4-phenyl-but-1-enyl)-5-oxo-pyrrolidin-1-yl]-heptanoic acid.

* * * * *